United States Patent [19]
Baldeschwieler et al.

[11] Patent Number: 6,080,586
[45] Date of Patent: *Jun. 27, 2000

[54] SUB-MICRON CHEMICAL IMAGING WITH NEAR-FIELD LASER DESORPTION

[75] Inventors: John D. Baldeschwieler; Jesse L. Beauchamp, both of Pasadena, Calif.; Marcel Widmer, Morges, Switzerland; Stephen D. O'Connor; Dmitri Kossakovski, both of Pasadena, Calif.

[73] Assignee: California Institute of Technology, Pasadena, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/628,875

[22] Filed: Apr. 5, 1996

[51] Int. Cl.[7] .............................. B01D 59/44; H01J 49/00
[52] U.S. Cl. ..................... 436/173; 436/181; 250/282; 250/288
[58] Field of Search .................................... 436/173, 181; 250/282, 288

[56] References Cited

U.S. PATENT DOCUMENTS 4,469,554   9/1984   Turner .

OTHER PUBLICATIONS

U. Boesl et al. *Int. J. Mass Spectrum. Ion Processes* 1992, 112, 121–166.
D. Van Labeke et al., *J. Opt. Soc. Am. A* 1993, 10 2193–2201.
S. McCulloch et al. *Meus. Sci. Technol*, 1995, 6, 1157–1162.
W. Tan et al. *Microchem. Proc. JRDC–KULTJ+. Int. Symp.* 1994, H. Masuhara, ed., North–Holland: Amsterdam Neth. pp. 301–318.
A.J. Meixner et al. *Opt. Eng.* 1995, 34, 2324–2332.
B. K. Furman et al. *Chem. Abstr.* 1982, 96, 45403g.
R. J. Perchalski et al. *Anal. Chem.* 1983, 55, 2002–2005.
J. D. Hogan et al. *Anal Chem.* 1991, 63, 1452–1457.
B.K. Furman et al. *Microbeam Anal.* 1981, 16, 336–338.
R.S. Brown et al. *Anal. Chim. Acta* 1991, 248, 541–552.
A. Lewis et al. *Anal. Chem.* 1991, 63, 625A–638A.
Z. Ma et al. *Rev. Sci. Instrum.* 1995, 66, 3168–3174.
J.W.P. Hsu et al. *Rev. Sci. Instrum.* 1995, 66, 3177–3181.
J.M. Behm et al. *Anal Chem.* 1996, 68, 713–719.
Ash and Nicholls (1972) Nature 237:510.
Betzig et al. (1992) Appl. Phys. Lett. 60:2484.
Betzig et al. (1991) Science 251:1468.
Bugg and King (1988) J. Phys. E: Sci Instrum. 21:147.
Chabala et al. (1995) International Journal of Mass Spectrometry and Ion Processes 143:191.
de Vries et al. (1992) Rev. Sci. Instrum. 63:3321.
Gaarenstroom (1993) Applied Surface Science 70:261.
Harootunian et al. (1986) Appl. Phys. Lett. 49:674.
Karas and Hillenkamp (1988) Anal. Chem 60:2299.
Maheswari et al. (1995) Journal of Lightwave Technology 13:2308.
Marchman et al. (1994) Rev. Sci. Instrum. 65:2538.
Overney (1995) TRIP 3:359.
Pangaribuan et al. (1992) Jpn. J. Appl. Phys. 31:1302.
Prutton et al. (1995) Ultramicroscopy 59:47.
Walther et al. (1992) J. Microscopy 168:169.
Zeisel et al. (1996) Appl. Phys. Lett. 68:2491.

*Primary Examiner*—Arlen Soderquist
*Attorney, Agent, or Firm*—Fish & Richardson P.C.

[57] ABSTRACT

The present invention discloses an improved method and apparatus for analyzing the surface of materials using submicron laser desorption gas phase analysis. The method uses a combination of Near-field Optical Microscopy and Time-of Flight Mass Spectroscopy.

11 Claims, 10 Drawing Sheets

SUB-MICRON CHEMICAL IMAGING WITH NEAR-FIELD LASER DESORPTION

FIELD OF THE INVENTION

The present invention relates generally to the field of surface chemical analysis. Specifically, the present invention includes a novel method and apparatus for analyzing the surface of a material using a combination of Near-field Optical Microscopy (NSOM) and Time-of-Flight Mass Spectrometry (TOF-MS).

BACKGROUND OF THE INVENTION

The ability to analyze the chemical composition of the surface of a material with sub-micron spatial resolution is integral to a number of scientific disciplines. A variety of techniques are currently used for surface chemical analysis with sub-micron spatial resolution, including X-ray Photoelectron Spectroscopy (XPS) (Gaarenstroom (1993) Appl. Surf. 70:261); Secondary Ion Mass Spectroscopy (SIMS) (Chabala et al. (1995) Int. J. Mass. 143:191) Scanning Electron Microscopy (SEM) (Walther et al. (1992) J. Vilicrosc. O. 168:169); Auger Electron Spectroscopy (Prutton et al. (1995) Ultramicros. 59:47) and Friction Force Microscopy (FFM) (Overney (1995) Trends Poly. 3:359). All of these methods probe some specific property of the material being analyzed to determine the chemical composition. XPS, for example, measures the X-ray atomic photoelectron emission spectra of the sample being analyzed. FFM probes the local lateral interaction (friction) between the sample and an AFM tip as it is scanned across the sample with the friction being dependent on the chemical composition of both the tip and sample. The spatial resolution currently obtainable using these methods varies from $1\mu$ for SIMS down to the Angstrom range for FFM. Unfortunately, the methods with the best spatial resolution, FFM and SEM, have poor chemical contrast.

Surface chemical analysis is also performed using spatially resolved mass spectrometry (MS). Spatially resolved mass spectrometry is currently conducted using an optically focused laser beam to desorb particles from the surface of the material being analyzed. (de Vries et al. (1992) Rev. Sci. Instrum. 63:3321–3325). Desorption is the process of removing particles from the surface of a material. The particles removed may be ions, atoms, molecules, clusters or larger structures. Once removed, the particles form a gas which is then analyzed to determine the composition of the material from which the particles were removed. Laser desorption generally refers to a technique in which photons provide the energy necessary to detach the particles from the surface of the material. Laser desorption is a "destructive analysis", in that, pieces of the material being studied are torn away during the analysis, thereby destroying the material.

Current laser desorption techniques can be briefly described with reference to FIG. 1. Referring to FIG. 1, a sample 5 has a surface 10 covered with particles 12. A light beam 15, such as a laser beam, is focused by optics 18 onto surface 10 to form an area of desorption 20. Particles 22 that are in the area of desorption 20 are detached from surface 10. An ionization beam (not shown) may pass above the surface 10 to ionize the desorbed particles 22.

In order to study the composition of a material by laser desorption, it is necessary that the light utilized be of the proper intensity and wavelength to remove the particles without destroying them. If the wavelength of the light is too short or the intensity is too high, particles 22 will likely undergo undesirable chemical reactions or be destroyed, rather than simply detach from the surface 10. On the other hand, if the wavelength of the light is too long or the intensity of the light is too weak, particles 22 will not detach from surface 10. The specific wavelength and intensity required will depend on the nature of the particles being removed. In general, light with a wavelength in the ultraviolet range is appropriate. The intensity of the light necessary is dependent upon the type of experiments being performed. For matrix-assisted laser desorption analysis (MALDI), an intensity of $10^6$–$10^7$ W/cm$^2$ is necessary. Matrix-assisted laser desorption ionization is a method for producing ions in the gas phase. It is especially useful for studying large biological molecules. (Karas and Hillenkamp (1988) Anal. Chem 60:2299). The molecules of interest are suspended in a matrix, such as sinapinic or dihydroxybenzoic acid, and irradiated with a short duration laser pulse (approximately 3 nanoseconds), at a frequency 10–30 Hz. Upon irradiation the embedded analyte is ionized without decomposition, and the ions can then be analyzed by mass spectroscopy. For metal desorption an intensity of $10^8$ W/cm$^2$ is necessary.

Although current laser desorption systems, such as those shown in FIG. 1, are able to provide the proper intensity and wavelength of light, it is difficult to achieve high spatial resolution with a laser. In this context, resolution refers to the accuracy in which the location of the particles being detached from the surface can be measured. As the resolution of the system is increased the determination of the location of the particles being detached from the surface becomes more accurate. In analyzing the composition of a subject material by laser desorption, it is important to be able to determine the location of particles being analyzed with a high degree of accuracy. Resolution is typically determined from the area of desorption (referred to as the spot size), which is the diameter of the laser beam on the surface. The smallest previously reported spot size is one micron, as discussed by deVries et al. (1992) Rev. Sci. Instrum. 63(6) :3321–3325.

Two restraints—namely, diffraction and economic feasibility—limit the ability to achieve resolutions less than one micron in current laser desorption systems. Diffraction refers to the departure from rectilinear propagation of light waves that is experienced by light resulting from some obstruction of the wave front by an opaque surface. As can be seen in FIG. 2A, unobstructed light travels in straight lines, referred to as rectilinear propagation, if the light is passed through an aperture which is roughly equivalent to the wavelength of the light, however, propagation beyond the barrier is no longer strictly rectilinear, but rather, the light penetrates into regions beyond the barrier into regions that cannot be reached by a straight line drawn from the source. This phenomenon is called diffraction. From a theoretical standpoint, the resolving power of an optical focusing system is restricted by the diffraction limit $4\lambda fo/\pi d$, where $\lambda$ is the wavelength, fo is the focal length of the lens and d is the beam width. To achieve high resolution with an optical focusing system high-precision lenses are required which are very expensive. Additionally, current laser desorption techniques require high precision optics to keep the laser narrowly collimated. These optics are expensive, and require time consuming precision alignment. Furthermore, different materials require different wavelengths to desorb. Therefore, when new materials are being studied the wavelength of the laser light must be changed. When the wavelength of the laser light is changed the optics must also be changed or resolution will be lost.

Spence et al. describes a more recent method for performing spatially resolved mass spectrometry in which the chemical composition of the surface is analyzed in one location at a time. Briefly, a scanning tunneling microscope (STM) tip is used to remove an atom (or group of atoms) from the sample being analyzed at a specific location. A high voltage pulse is then applied to the top to desorb and ionize this atom(s). The atom(s) is then guided to a Time-of Flight (TOF) detector to analyze its mass. The drawback of this method is that the system probes the sample in a single location only, leaves the surface to perform the mass spectral analysis and has to be returned to the surface with Angstrom reproducibility. This method leads to a number of technical problems and long analysis times, if surface mapping is the goal.

The methods of surface analysis currently available are not able to provide both high spatial resolution and the detailed chemical information that is desired. There is always a trade-off between resolution and chemical contrast, in that methods which provide high spatial resolution are unable to provide the detailed chemical information that is desired and methods which provide detailed chemical information lack the resolution that is desired. There remains a need, therefore, for a method of conducting surface analysis which provides both high spatial resolution and a detailed chemical analysis of the surface being studied.

Near-field scanning optical microscopy (NSOM) is a probe microscopy technique that was invented in 1972, as discussed by Ash et al. (1972) Nature 237:510. In NSOM a beam of light is passed through an aperture which is smaller than the wavelength of the light to optically and non-destructively image features on a surface. When substantially collimated light passes through an aperture which is smaller than the wavelength of the light, the light is spread out into what is referred to as a Fraunhofer diffraction pattern (see FIG. 2B). Referring to FIG. 2B, when substantially collimated light 35 strikes an opaque surface 40 and passes through an aperture 42, that is smaller than the wavelength of the light, a classical diffraction pattern 47 appears in the far-field 45, however, in the near-field 50, the light remains generally collimated to the size of aperture 42. Far-field 45 is generally the region more than one wavelength from the aperture. Near-field 50 is the region substantially less than one wavelength from aperture 42, and is approximately equal to the width of aperture 42. Thus, in the near field the illuminated area does not depend upon the wavelength of light, but rather depends only on the size of the aperture. NSOM uses this effect to perform optical microscopy with sub-wavelength resolution. The best reported spatial resolution using NSOM is approximately 20 nm.

The heart of any probe microscopy instrument lies in the shape of the tip of the probe. In NSOM, a sub-wavelength aperture must be constructed and scanned over the surface of the sample. Harootunian et al first developed tapered NSOM tips in 1986 by pulling quartz micro pipettes down to a point, followed by coating the outside of the pipettes with evaporated aluminum. (Harootunian et al (1986) Appl. Phys. Lett. 49:674). Betzig et al. have since found that quartz fiber optics serve this purpose even better. (Betzig et al. (1991) Science 251:1468). The fiber optics have a natural degree of collimation along the propagating axis, resulting in a larger amount of light reaching the end of the tip, which enhances the intensity for smaller and smaller aperture sizes.

It is an object of the present invention to provide a laser desorption technique and apparatus which provides high spatial resolution together with a detailed chemical analysis of the surface being analyzed.

Another object of the present invention is to provide a laser desorption technique and apparatus that is easy and inexpensive to construct and operate.

A further object of the present invention is to provide a stable laser beam for laser desorption.

Yet another object of the present invention is to provide a laser desorption technique and apparatus which desorbs in a spot with a size which is wavelength independent.

Even another object of the present invention is to utilize methods from near-field scanning optical microscopy and time-of-flight mass spectrometry to achieve the above objects.

Additional objects and advantages of the invention will be set forth in the description which follows and in part will be obvious from the description, or may be learned by the particulars of the invention. The objects and advantages of the invention may be realized and obtained by means of the instrumentalities and combinations particularly pointed out in the claims.

SUMMARY OF THE INVENTION

The present invention involves the application of near-field scanning optical microscopy techniques to laser desorption. Included in the present invention is an improved method and apparatus for performing laser desorption gas phase analysis. The present invention is directed to an apparatus having a probe with a sub-wavelength aperture. Light from a source is projected through the aperture to form a near-field zone. The apparatus has a means for moving the surface of a sample into the near-field zone. The wavelength and intensity of the light is suitable for desorbing particles from the surface, if the surface is within the near-field zone.

The method of the present invention includes providing a source of light and projecting the light through an aperture to form a near-field zone. A surface of a sample is moved into the near-field zone. The wavelength and intensity of the light is selected to cause particles to desorb from the surface when the surface is within the near-field zone.

The probe may be a solid fiber or a hollow pipette having a tapered tip with opaque sides and a transparent face. In a preferred embodiment of the present invention the apparatus is designed to prevent the solid fiber probe aperture from becoming blocked by retracting the aperture from the surface and applying an additional light pulse which will desorb particles from the aperture, but not the surface. The apparatus prevents the pipette probe aperture from becoming blocked by accumulating the desorbed particles on the inside surface of the pipette tube. It is possible to create a desorption spot size approximately equal to or less than one-hundred nanometers wide with the present invention. Once desorbed the particles are vaporized and analyzed by means known to those in the art such as, infrared spectroscopy or time-of-flight mass spectroscopy. In the preferred embodiment the vaporized particles are analyzed by time-of-flight mass spectroscopy.

The method and apparatus of this invention have many uses, particularly in the area of material science, biology and forensic studies. Any use in which surface analysis of a material is required is with the scope of this invention. Applications include surface chemical characterization, macromolecule desorption and microelectronic applications.

BRIEF DESCRIPTION OF TIE DRAWINGS

The accompanying drawings, which are incorporated in and constitute a part of the specification, schematically illustrate a preferred embodiment of the invention, and together with the general description given above and the detailed description of the preferred embodiment given below, serve to explain the principles of the invention.

DETAILED DESCRIPTION OF THE INVENTION

The present invention includes an improved apparatus and method for performing laser desorption gas phase analysis. Specifically, the present invention involves the application of near-field scanning optical microscopy techniques in conjunction with time-of-flight mass spectrometry (TOF-MS) to analyze the chemical composition of surfaces with significantly greater resolution than previously reported. The improved apparatus of the present invention is comprised of a probe, having a sub-wavelength aperture, which is used to create a near-field zone. The improved resolution of the present invention is achieved by performing the desorption in the near field zone where the light remains highly collimated to approximately the width of the aperture. This obviates the need for expensive optics to achieve high resolutions. This also obviates the need to change the optics each time a new material is being studied.

The improved method of the present invention is comprised of: providing a source of light of the proper wavelength and intensity, projecting the light through an aperture to form a near field zone, positioning a sample to be analyzed within the near-field zone; irradiating the sample with the light to desorb particles from the surface of the sample; analyzing the desorbed particles to determine the chemical composition of the sample.

Figure 3:
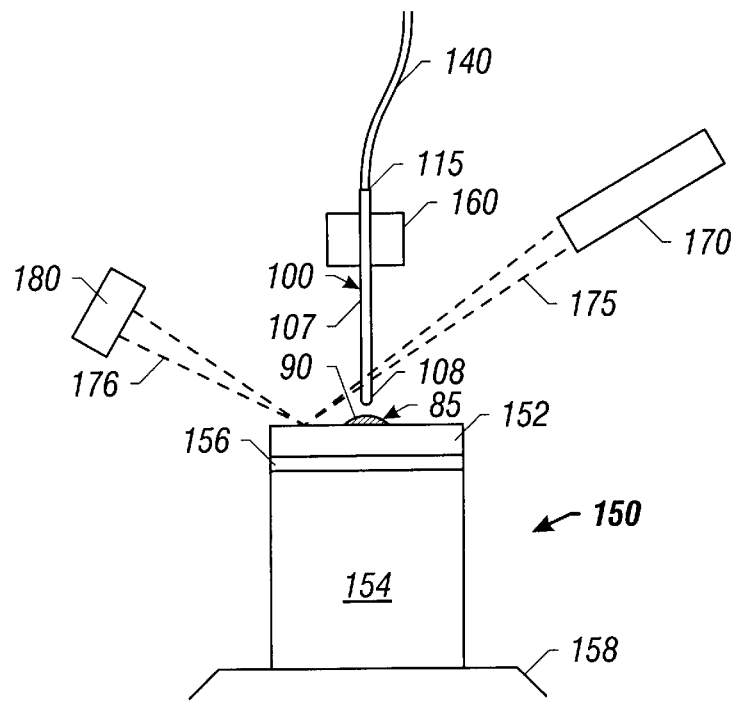
FIG. 3 is a schematic diagram of a device to conduct laser desorption according to the present invention.

One embodiment of the apparatus of the present invention is illustrated in FIG. 3. Referring to FIG. 3, a probe 100, having a body 107 and a tapered tip 108, is coupled to a fiber optic cable 140 which carries collimated light from a source of collimated light, such as a laser (not shown) into the probe 100. Probe body 107 conducts the light from the fiber optic cable 140 to an aperture 108 at the tip of the probe. The tapered tip 108 acts as a funnel to channel as much light as possible through the aperture and onto a sample of the material to be analyzed. To ensure that the light is contained, the outside surfaces of tip 108 may be coated with a reflective layer, such as a metal selected from gold or aluminum.

A sample 85 of the material to be analyzed is placed on a sample mount 150. Sample 85 has a surface 90 facing the tapered tip 108 of probe 100. The sample is attached to mounting surface 152. The position of the sample relative to the probe 100 is controlled by a scanning mechanism 154 attached to the mounting surface 152 by a macor spacer 156. In a preferred embodiment the scanning mechanism is a piezoelectric crystal. Most preferably the scanning mechanism is a cylinder of piezoelectric ceramic, such as lead zirconium titanate. As is well known, a piezoelectric material expands when an electric potential is applied across the material. The base of the piezoelectric crystal 154 (also called the piezoscanner 154) is attached to an immobile frame 158. A set of electrodes (not shown) plate sections of the inside and outside of the piezoscanner tube 154. By controlling the voltage applied to the various sections of piezoscanner 154, the length and flexure of the piezoscanner 154 can be precisely controlled, which enables the movement of sample 85 in three dimensions to precisely position sample 85 relative to the tip of the probe 108. In the preferred embodiment, the macor spacer is composed of dielectric material, has the same diameter as the piezoscanner 154, and is one-sixteenth to one-thirty-second inch thick.

Figure 4:
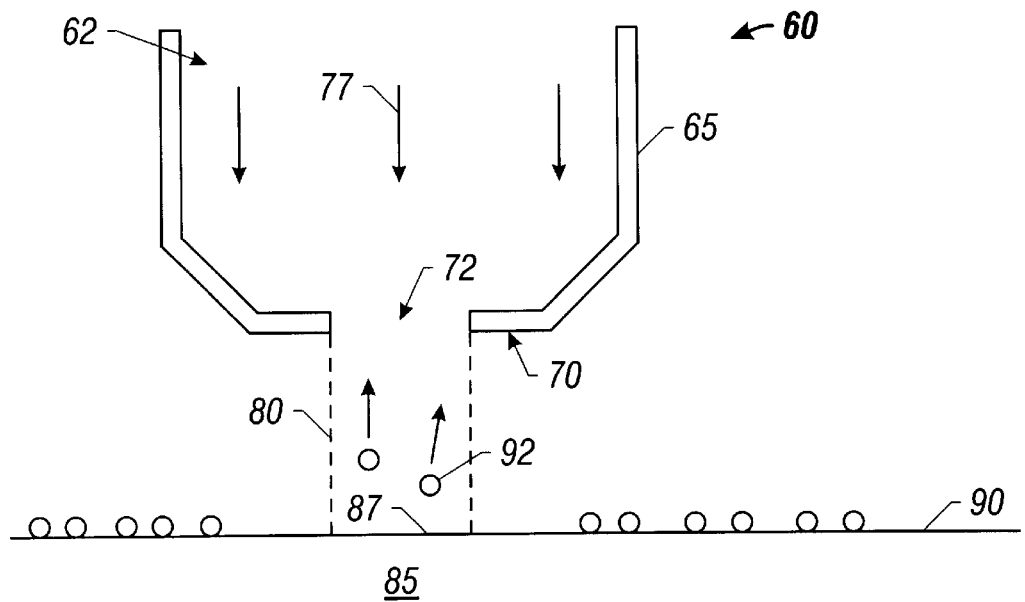
FIG. 4 is a schematic illustration of a laser desorption probe having an aperture according to the present invention.

FIG. 4 illustrates in greater detail a laser desorption probe according to one embodiment of the present invention. As shown in FIG. 4, the elongated probe 60 has an interior region 62, which transmits light and an opaque surface 65 which prevents light from escaping from the interior region 62 of the probe. To ensure a sufficient intensity of light at the desorption spot, the light must be contained inside the tube. Light can be blocked from exiting through surface 65 by standard means well known to those in the art, for example by use of an optical effect, such critical angle reflection, or by use of an opaque coating, such as a metal selected from aluminum or gold. The forward face 70 of the probe 60 is tapered to a narrow aperture 72 through which light may pass. In operation, light 77 passes through interior region 62 and aperture 72 to form a light beam 80 which strikes the surface 90 of the sample 85 to be analyzed on spot 87. Aperture 72 need not necessarily be a physical gap in probe 60. However, aperture 72 must be a region substantially transparent to the wavelength of light 77 surrounded by a region which is opaque to the wavelength of light 77.

When the light 77 hitting the surface of the material to be analyzed is of the proper wavelength and intensity, particles 92 are desorbed from desorption spot 87. The intensity of light on spot 87 is dependant upon the distance between the aperture 72 and the surface 90 of the material being analyzed. The smaller the distance, the higher the intensity. As described above, the intensity necessary at the surface to cause particles 92 to be desorbed is approximately $10^6$–$10^8$ W/cm$^2$. Additionally, the wavelength of the light necessary to induce desorption without destroying the particles 92 being desorbed is typically in the ultraviolet range. The exact wavelength will depend on the type of the particles being desorbed and can be readily determined by those skilled in the art.

Figure 1:
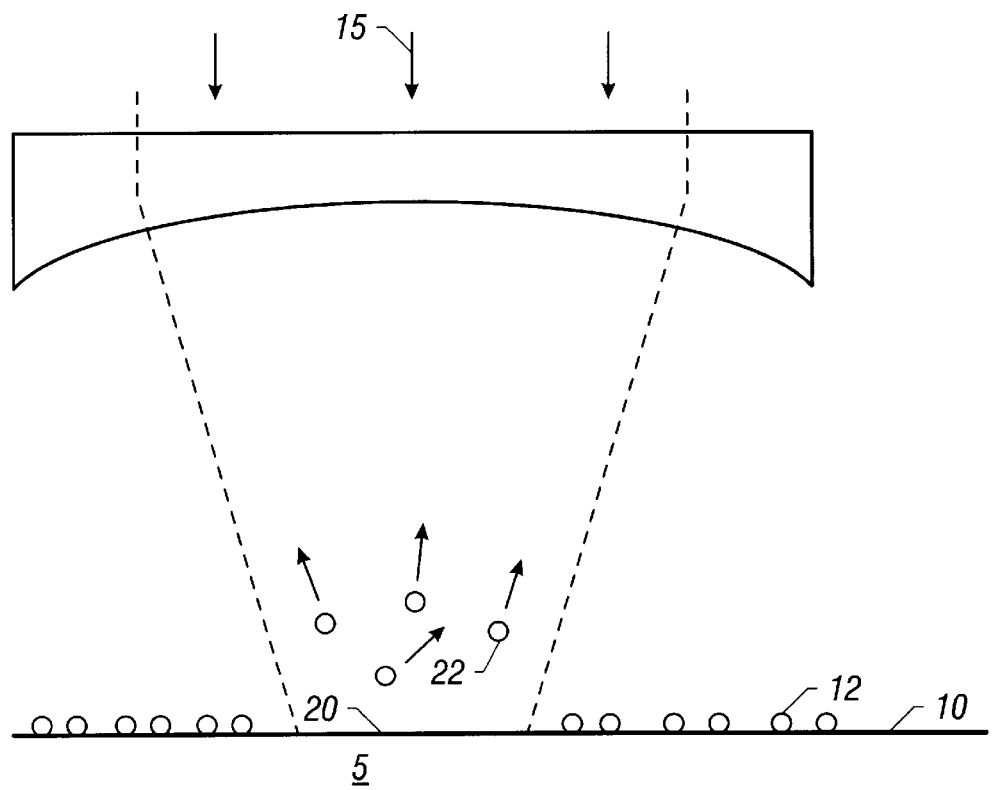
FIG. 1 is a schematic representation of laser desorption of molecules from a surface according to the prior art.
Figure 2A:
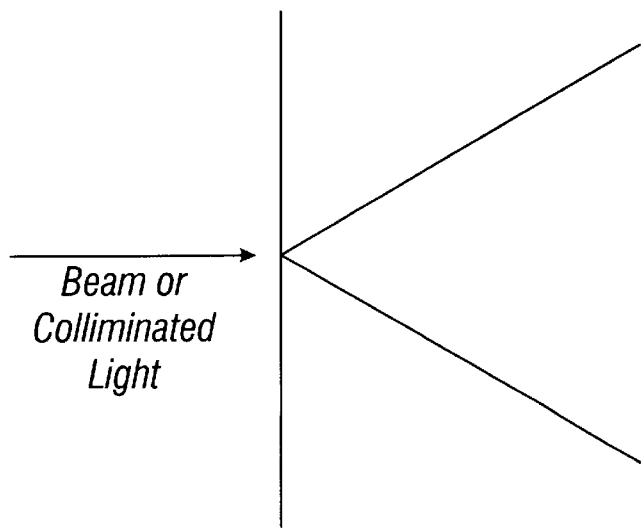
FIG. 2A is a schematic illustration of classical diffraction.
Figure 2B:
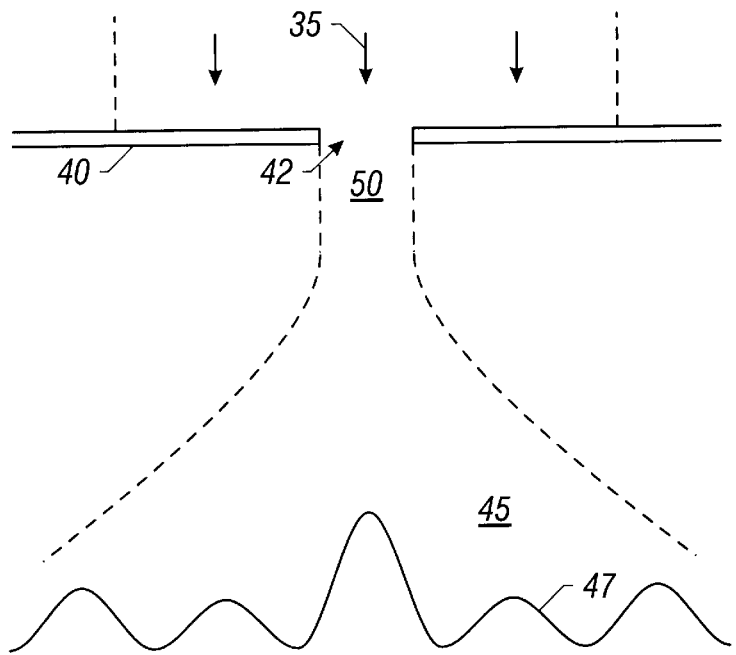
FIG. 2B is a schematic illustration of a Fraunhofer diffraction pattern.

The surface 90 of the material being studied is positioned, using the scanning mechanism, within the near-field zone 50 (FIG. 2) where light beam 80 remains collimated to approximately the width of aperture 72. The length of the near-field zone 50 (FIG. 2) is approximately equal to the radius of the aperture. In a preferred embodiment the tip of the probe is positioned at a distance approximately equal to the radius of the aperture from the surface of the material being analyzed. When using a light source with a wavelength of about 340 nanometers, aperture 72 should be less than one-hundred nanometers wide, and preferably less than forty nanometers. For a thirty-five nanometer aperture, the near-field 50 extends out from the aperture about fourteen nanometers.

Figure 5A:
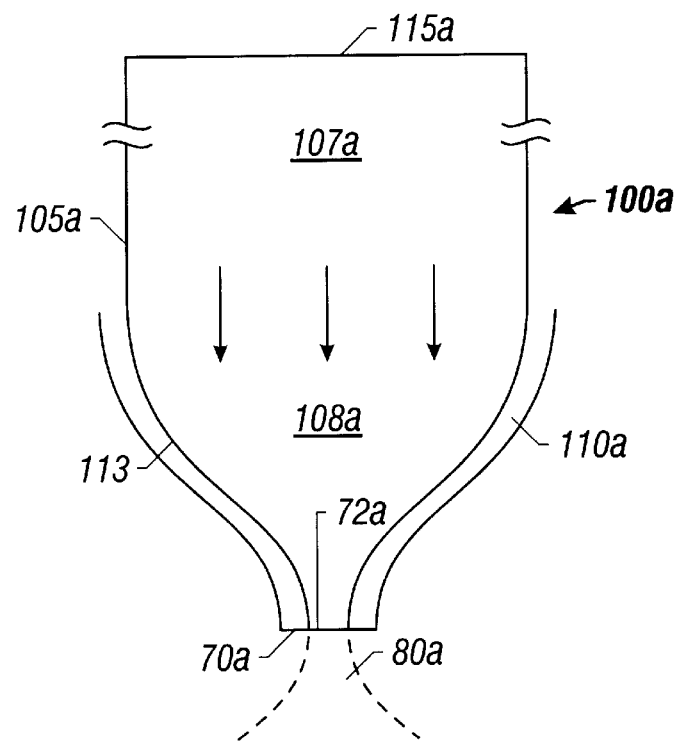
FIG. 5A is a schematic sectional side-view of a probe using a fiber.

As stated above, there are currently two types of probes used in NSOM—micro pipettes and solid fiber optic probes. (Betzig et al. (1991) Science 251:1468). FIG. 5A depicts a solid fiber optic probe 100a. Fiber optic probes have a natural degree of collimation along the propagating axis, resulting in a larger amount of light reaching the end of the tip. The optical fiber consists of an inner core 105a with a first refractive index and an outer cladding with a second refractive index 105b (see FIG. 5B). Fiber 105a is composed of transparent material such as glass or quartz. Quartz is the preferred material. Unlike prior art fiber optic probes used in NSOM, which are tuned for visible light, the fiber optic probe 100a is tuned for ultraviolet light, preferably for 337.1 nanometers. The fiber is tuned for maximum internal reflection at a particular wavelength by adjusting the refractive indices and diameters of the core and cladding, as would be easily accomplished by one skilled in the art. In a preferred embodiment fiber 105a is a single mode fiber having a core diameter of 5–10 microns.

The tip 108a of the probe is tapered to a diameter at aperture 72a of less than five-hundred nanometers. In a preferred embodiment the tip 108a of the probe is tapered to a diameter of less than one-hundred nanometers. The tip may have a diameter of less than thirty nanometers and can be as small as ten to fifteen nanometers. The tapered tip 108a has a length of less than five millimeters, preferably about one millimeter. The body 107a can be up to a meter long. Cone angles in the range of 20–40 degrees are preferred. To prevent sideways scattering of light from the tapered tip 108a, the outer surface 113 of tip 108a may be coated with a reflective coating 110a to keep the light inside the fiber 105a. Coating 110a may be aluminum deposited to a thickness of about a thousand angstroms. Other metals, such as gold, may be used in place of aluminum. The total thickness of coating 110a depends on the reflectivity and transmitivity of the coating, and should be sufficient to ensure that the coating is opaque. Optionally, coating 110a may also cover body 107a of tube 105a.

The fiber optic tip can be prepared by any method known in the art. (See, e.g., Marchman et al. (1994) Rev. Sci. Instr. 65:2538; Maheswari et al. (1995) J. Lightwave Techn. 13:2308) In one embodiment of the present invention fiber probe 100a is prepared using the fiber heating and pulling technique reported by Betzig et al. (See Betzig et al. (1992) Applied Physics Letters 60:2484–2486; Betzig et al. (1991) Science 251:1468, which are incorporated herein by reference). Briefly, a standard quartz fiber, such as an optical fiber from Radient Co. is heated with a $CO_2$ laser to decrease the viscosity of the fiber. While the fiber is being heated, it is pulled with a spring mechanism, such as a commercial pipette puller from Sutter Instruments, to stretch the tip out to a point. Fibers with an external tip diameter of less than one-hundred nanometers, and down to twelve nanometers, may be formed reproducibly using this method.

Special care must be taken in tapering the tip 108a of the probe. If the tapered portion is too long, the light being transmitted through the tip will be reflected back or heat dissipated prior to exiting the aperture. Because the reflective layer absorbs a portion of the light at each bounce, a large amount of light will be lost and the intensity may be too low to cause desorption. On the other hand, if the tapered portion is too short, then too much light will reach the aperture and the intensity will be too high and will cause undesired chemical reactions on the surface of the material being studied. Additionally, if the tip is small and the light intensity is high, there is a danger that the reflective metal coating will be burned off by the ultraviolet radiation, thereby destroying the effectiveness of the probe. This is not a concern in standard NSOM, which uses lower energy visible light, rather than ultraviolet light used for desorption. As stated above the length of the tip should be less than 5 millimeters, preferably 1 millimeter and should taper with a cone angle in the range of 20–40 degrees.

After pulling the fiber, the non-tapered end of the fiber is cleaved to produce a smooth back face 115a. The amount of tension placed on the fiber to produce a smooth face when it is cleaved can readily be determined by those skilled in the art. After the non-tapered end of the fiber is cleaved, the backface 115a is polished to remove surface defects and create a mirror-like surface.

In a second embodiment of the present invention, fiber probe 100a is prepared using selective fiber etching with a buffered etching solution as reported by Pangaribuan et al. (1992) Jpn. J. Appl. Phys. 31:1302–1304. Briefly, one end of the fiber is placed in a buffered etching solution, which targets the difference in the chemical composition of the fiber core and cladding. By careful control of etching time and solution composition it is possible to make a sharp tip which tapers -with a cone angle in the range of 20–40 degrees.

In a preferred embodiment, the probe is prepared using yet another method of fiber etching. A protective layer of organic solvent is placed on top of an etching solution, HF or buffered HF. The organic layer prevents evaporation of the HF and limits the upward propagation of HF along the fiber due to capillary forces. The contact angle at the interface is dependent on the mutual wetting characteristics of all three media. The etching stops at the solvent/etchant interface. The technique is very simple and exact timing is not critical, because when the etching stops the taper is protected in the organic layer. The cone angles achieved using this technique are in the range of 15–40 degrees. The organic solvent may be selected from the group consisting of octyl alcohol, benzene, 1-chlorobutane, and 2,6,10,14-tetramethylpentadecane (TMPD). In a preferred embodiment the organic solvent is tetramethylpentadecane (TMPD), which gives a cone angle of approximately 19 degrees.

Finally, the tip of the probe may optionally be coated with an opaque layer to prevent loss of light from the side of the tapered region of the probe. Any reflective metal may be used, but aluminum is preferred because it has one of the highest reflection coefficients at 337.1 nanometers and because it is inexpensive and easy to deposit. The metal may be deposited by angled evaporation to coat only the sides of the tube, and not the forward face 70a.

The apparatus 130 used to coat the tips of the fiber optic probes consists of rotating tip holders, a tungsten boat and a source of high current. The apparatus is enclosed within an evaporation chamber. The tips are rotated on the rotating tip holders during coating to ensure smooth homogeneous coating. Aluminum pieces are put into the tungsten boat which is heated by a high current source (approximately 25 Amp). The evaporation chamber is pumped down to $1 \times 10^{-5}$ Torr. At this pressure the mean free path is about 1 meter and the evaporated atoms easily reach the tips in a highly directional fashion. Up to 12 tips can be coated during a single run of the evaporator.

Figure 5B:
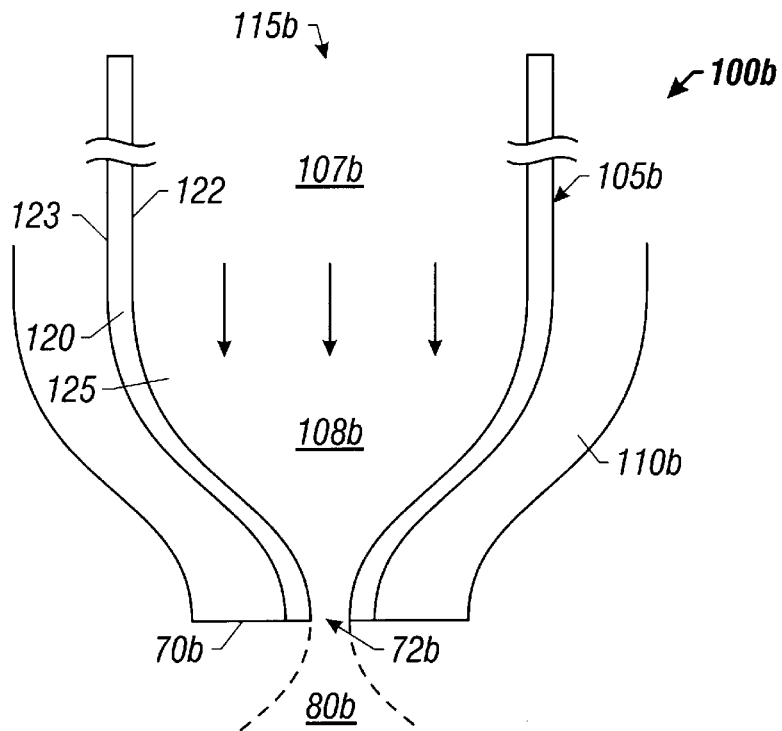
FIG. 5B is a schematic material side-view of a probe using a quartz pipette.

FIG. 5B depicts a probe 100b in which the transparent tube 105b is a pipette, rather than a fiber. Tube 105b is composed of a transparent material such as glass or quartz. Quartz is preferred because it is less likely to break when pulled. Tube 105b is a hollow cylinder 120 with an interior surface 122, an exterior surface 123, and an interior region 125. The body 107b of tube 105b is about one to five millimeters in diameter. Tip 108b of tube 105b is tapered to a diameter less than five-hundred nanometers, more preferably about one-hundred nanometers. The taper length of tip 108b is less than five millimeters, and is preferably about one millimeter. Similar to the fiber 105a, the outer surface 123 of tip 108b will not contain the light and must be coated with a reflective layer 110b. However, unlike fiber 105a, the body 107b of pipette 105b also does not naturally contain and collimate light. Therefore, it is necessary to provide some means of preventing light from escaping from body portion 107b. In one embodiment, exterior surface 123 of the entire body 107b is coated with a reflective layer 110b, such as aluminum. In a second embodiment, a lens (not shown) may be placed to focus and keep a laser beam (not shown) inside of the interior surface 122. In a preferred embodiment, shown in FIG. 5C, an optical fiber 127 having a flat face 126 is placed in interior region 125, to prevent light from escaping. Optical fiber 127 has the same characteristics as fiber 105a, except that it has a flat face 126 instead of a tapered tip. A clearance of one centimeter or less between the flat face 126 and the aperture 72b is preferred.

In one embodiment of the invention, the reflective layer 110b extends at least to the focal point of the laser beam. In the preferred embodiment, the reflective layer 110b extends at least to the flat face 126 of optical fiber. Optionally, a bonding metal layer may be deposited as part of coating 110b to act as an adhesive between the reflective metal and the tube 105b.

Probe 100b may be prepared using a technique described by Harootunian et al. (1986) App. Phys. Lett. 49:674, incorporated herein by reference. Briefly, a standard glass pipette is heated and pulled with a pipette puller. The metal layers are angle evaporated onto the outer surface 123 to a thickness of about five-hundred nanometers. A bonding layer is not necessary if the coating 110b is evaporated slowly under clean conditions. Because tube 105b is hollow, there is an open end 115b rather than a smooth face 115a. Fiber 127 may be inserted into the open end 115b until the blunt face 126 is approximately one centimeter from the aperture 72b.

Referring back to FIG. 3, if probe 100 is a fiber optic probe (FIG. 5A), then the cable 140 may be the body 107a of the probe (FIG. 5A). If probe 100 is a pipette probe (FIG. 5B), then the cable 140 may be inserted into the open end 115b as optical fiber 127 and bonded in place (FIGS. 5B and C).

In operation, the tip 108 of probe 100 remains relatively motionless, while the piezoscanner 154 moves the sample 85. The piezoscanner 154 first moves the surface 90 of sample 85 into near-field zone of light beam 80 (see FIG. 4). Selection of the exact distance between the tip 108 of the probe and surface 90 of the material being analyzed, depends upon the intensity of the light in the body 107 of the probe, the efficiency of light transmission of the tip 108 of the probe, and the desired intensity at surface 90. This distance may be experimentally determined, but will be within the near-field zone. In a preferred embodiment, a nitrogen laser, purchased from Laser Science Inc. (Newton, Mass.) (not shown) is activated and a light pulse desorbs molecules from a particular point on the surface of the sample. The laser emits at a wavelength of 337.1 nm and has a 3 nanosecond pulse duration delivering 250 µJ. The piezoscanner 154 then moves the sample 85 horizontally so that a new point on the surface 90 is beneath the tip 108 of the probe. The steps of moving the sample 85 and pulsing the laser may be repeated as many times as desired. Finally, the piezoscanner 154 retracts sample 85 away from the probe 100.

Because the surface 90 of the material being analyzed is in the near-field zone 80, the light beam does not spread substantially from aperture 72 before striking surface 90. Consequently, desorption spot 87 will be approximately the same size as aperture 72. For example, if aperture 72 is one-hundred nanometers in diameter, spot 87 will be approximately one-hundred nanometers wide. Compared to the prior spot size of one micron, the one-hundred nanometer desorption spot size represents a ten-fold increase in resolution. In a preferred embodiment the aperture 72 is 50 nanometers wide. Aperture 72 may, however, be as small as 12 nanometers wide, resulting in close to a one-hundred-fold improvement in resolution.

In order to fully exploit the near-field effect the distance between the sample and the tip of the probe will preferably be accurately monitored and maintained at ten to one-hundred nanometers. This can be accomplished by means of a variety of feedback mechanisms, including but not limited to the measurement of the shear force between the tip and the sample (Betzig et al. (1992) Appl. Phys. Lett. 60:2484, incorporated herein by reference) or the measurement of capacitive feedback between the tip and the sample (Bugg and King (1988) J. Phys. E. Sci. Instrum. 21:147). Other feedback mechanisms will be apparent to those skilled in the art.

Means to measure the shear force and determine the distance between the tip and the sample are illustrated in FIG. 3. As shown in FIG. 3, the probe 100 is attached to a dithering piezoelectric crystal 160. The dithering piezoelectric crystal 160 vibrates the base of the probe 100 parallel to the surface 90 of the sample 85. The dithering piezoelectric crystal 160 is attached to probe 100 less than three inches, and preferably one centimeter, from tip 108. The dithering piezoelectric crystal 160 drives the probe at its resonance frequency, with a spacial amplitude of several angstroms. A typical resonance frequency is 7 kHz, and a typical applied amplitude is 10 Å. Because the probe body 107 is long and thin, resonance tip 108 will undergo a large swing in response to a small applied vibration of the base. The probe has a Q-factor (the change in tip amplitude divided by the driving amplitude) as high as two hundred. The longer the probe 100 (in terms of the distance from the tip 108 to the mounting on the dithering piezoelectric crystal 160), the higher the Q-factor. When the tip approaches the sample, the local shear interactions cause a slight change in the resonance frequency. As a result, the probe is no longer driven at resonance, and the amplitude and phase of motion of the tip decreases.

Figure 6:
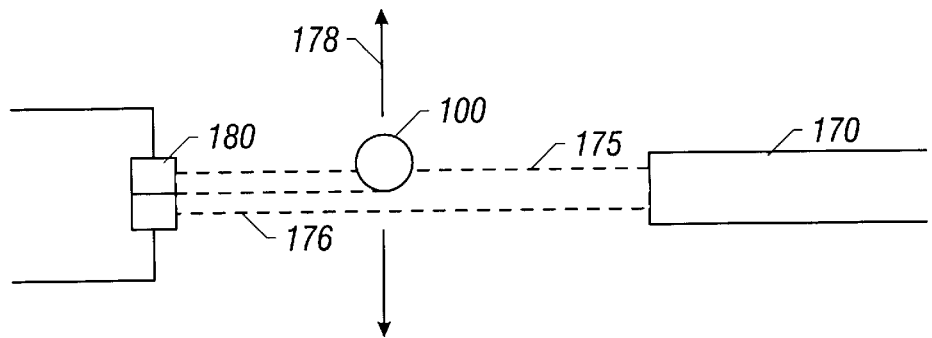
FIG. 6 is a schematic diagram of a feedback mechanism to measure the distance between the top and the surface.

The change in motion of the tip can be measured optically, as illustrated in FIGS. 3 and 6. Referring to FIG. 3, a laser 170 is used to create a focused beam 175, which is positioned to be partially obstructed by probe 100. Laser beam 175 strikes probe 100 perpendicular to the direction of vibration 178 and at a sixty degree angle to the tube shaft axis (see FIG. 6). The unblocked portion 176 of the laser beam reflects off the sample mount 156 into a two-quadrant photodiode 180. If the tip 108 of the probe is far from the sample 85, the tip 108 vibrates with a large amplitude, but if the tip 108 is nearer the sample 85, the probe 100 is decoupled from the resonant frequency and the tip 108 vibrates with a small amplitude. The photodiode monitors the relative dithering response. The phase variation and amplitude damping can be monitored with a lock-in amplifier (not shown).

The shear-force feedback system may be used while the desorbing laser is activated. Since the probe 100 is decoupled from resonance when the surface 90 is in the near-field zone, the motion of the aperture 72 in tip 108 of the probe is only a few angstroms. In comparison, the total width of the aperture 72 is typically at least one-hundred angstroms. Thus, the shear-force feedback system increases the size of the desorption spot 87 by only a few percent.

Figure 7:
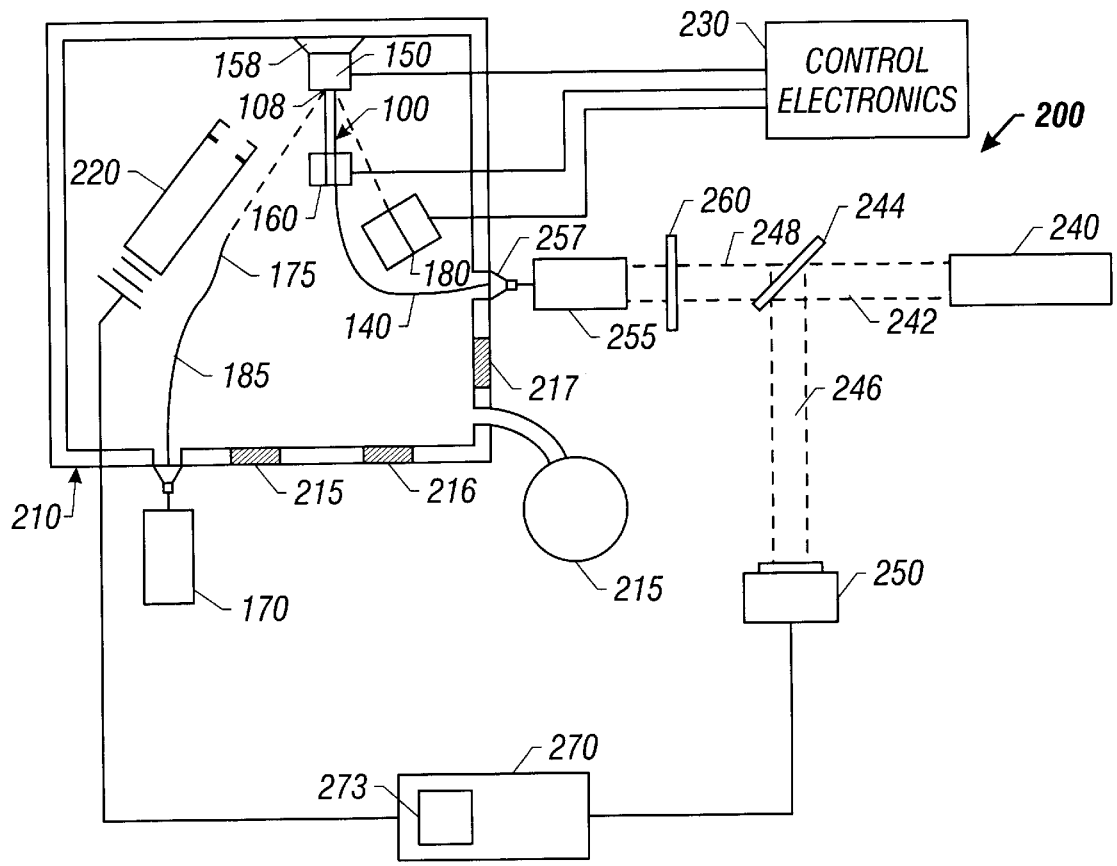
FIG. 7 is a schematic diagram of an apparatus to conduct gas-phase molecular analysis according to the present invention.

FIG. 7 shows a complete apparatus 200 for conducting gas-phase molecular analysis according to one embodiment of the present invention. Sample mount 150, probe 100, and dither piezoelectric crystal 160 are located inside a vacuum chamber 210. A pump 215 removes the atmosphere from the vacuum chamber 210. Vacuum chamber 210 also contains a molecular analyzer 220.

During desorption, light from probe 100 will ionize desorbed particles. The ions fly randomly into vacuum chamber 210. The percentage of particles that are ionized, and whether the particles are positively or negatively charged, depends on the nature of the particles. The type and amount of ionization caused by the light beam may be experimentally determined by those skilled in the art.

Electric fields direct the ions into analyzer 220. Analyzer 220 may be a mass spectrometer, a chemical spectrometer, or any other instrument used to measure a physical property of the molecules that are desorbed from the sample. If the analyzer is a mass spectrometer, then it may use sectors, quadropoles, ICR, or time of flight. Time of flight mass spectrometry is preferred because it is simple and has a fairly high mass detection limit.

Elements of the feedback mechanism may be placed outside or inside the vacuum chamber 210. Preferably, a laser 170 located outside the chamber is connected to an optical fiber 185 located within the vacuum chamber 210. Optical fiber 185 runs through the wall of vacuum chamber 210 and shines laser beam 175 at tip 108 of probe 100. The laser beam 175 is at a sixty degree angle to the probe axis. The partially blocked beam reflects off of the sample mount 150 and into a photodetector 180. The photodetector 180, dithering piezoelectric crystal 160, and piezoscanner electrodes are all electrically connected to control electronics 230. Control electronics 230 control the horizontal and vertical motion of the piezoscanner by controlling the voltage and applied across the piezoelectric crystal. Control electronics 230 also measure the feedback response measured by photodetector 180, as the piezoscanner 150 moves the sample 85 closer to tip 108 of probe 100. Alternately, the laser beam 175 could shine through a quartz window 215, or the laser 170 could be inside vacuum chamber 210. Preferably, photodetector 180 is located inside of the vacuum chamber 210, but alternately, reflected laser beam 176 could shine through a quartz window 216 into photodetector 180 outside vacuum chamber 210.

A laser 240 provides the collimated light necessary for desorption. Preferably, a nitrogen laser operating at 337.1 nanometers is used, but other lasers which produce light in the range of three hundred to three hundred and sixty nanometers may also be used. Other wavelength lasers may be used in conjunction with a wavelength filter (not shown). The laser 240 creates a laser beam 242 which is divided by beam splitter 244 into two beams 246 and 248. Beam 246 is reflected toward a pyro-detector 250. Beam 248 passes through splitter 244 and hits an optical coupler 255. Optical coupler 255 directs the light in beam 248 into an optical fiber 140. Optical coupler 255 may be an Oz Optics coupler. Optical fiber 140 directs the light to probe 100.

Optical coupler 255 may be located either inside (not shown) or outside of the vacuum chamber 210. If optical coupler 255 is inside the vacuum chamber 210, then the laser beam 248 is directed through a quartz window 217 in chamber wall 210 and onto the coupler 255. If the optical coupler is outside chamber 210, then a feedthrough 257 is needed to introduce optical fiber 140 into vacuum chamber 210. It is preferred to place coupler 255 outside of the vacuum chamber 210 because if optical fiber 140 becomes misaligned during pumping, the experiment must be restarted. A Teflon pink-clamp feedthrough 257 is very efficient and allows the vacuum chamber to reach pressures at least as low as $10^{-7}$ Torr.

As described above, the intensity of light striking the sample being analyzed must be of sufficient wavelength and intensity to cause desorption without destroying the desorbed particles. At least two methods may be used to control the intensity of light in the body of the probe 100. First, an attenuation filter 260 may be placed between the laser 240 and coupler 255, either in beam 242 or beam 248. Second, the optical fiber 140 may be partially decoupled from the optical coupler 255. Fiber 140 begins physically uncoupled from coupler 255. The intensity of the light is controlled simply by moving the coupler toward the face of the fiber until the intensity is just sufficient to cause desorption.

The analyzer 220 and pyro-detector 250 are connected to detection electronics 270 which synchronizes the laser pulse to the pulses from analyzer 220. Detection electronics 270 may include a display 273. Detection electronics 270 may be an oscilloscope, such as a Wavetek.

Unlike NSOM, during laser desorption, molecules and larger particles are dislodged from the surface and may accumulate on nearby objects. It is important to maintain the integrity of the tip 108 of the probe during the experiments. When aperture 72 is very close to the surface 90 during desorption, a large percentage of the desorbed ions may strike the tip 108. If a large number of particles strike aperture 70, it may become blocked and not pass sufficient light to cause desorption.

Figure 5C:
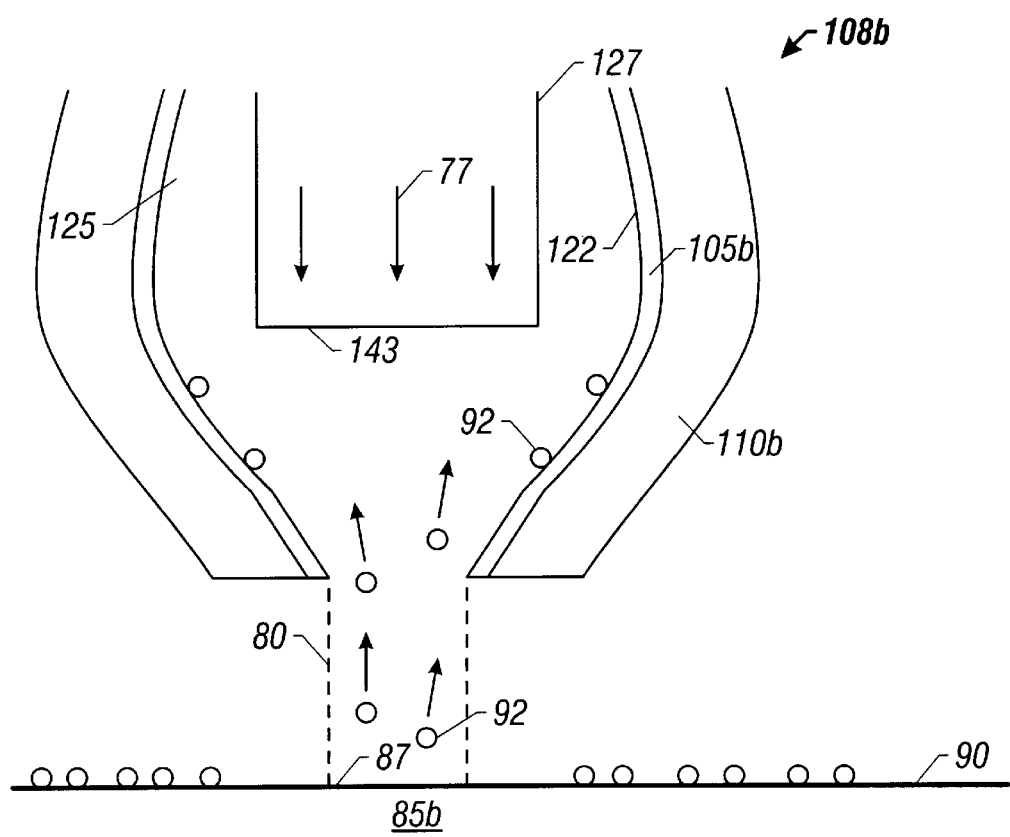
FIG. 5C is a schematic illustration of the use of a probe with a quartz pipette to avoid blocking the aperture.

One method to prevent particles from blocking the aperture of a pipette probe is to use hollow tips as illustrated in FIG. 5C. An optical fiber 127 is inserted into the probe cavity 125 to carry light 77 to the aperture 72. A clearance of about one centimeter should be maintained between the face 126 of fiber 127 and aperture 72. The desorbed ions 92 will attach to interior surface 122 and will not reach the face 126 of optical fiber 127.

Figure 8A:
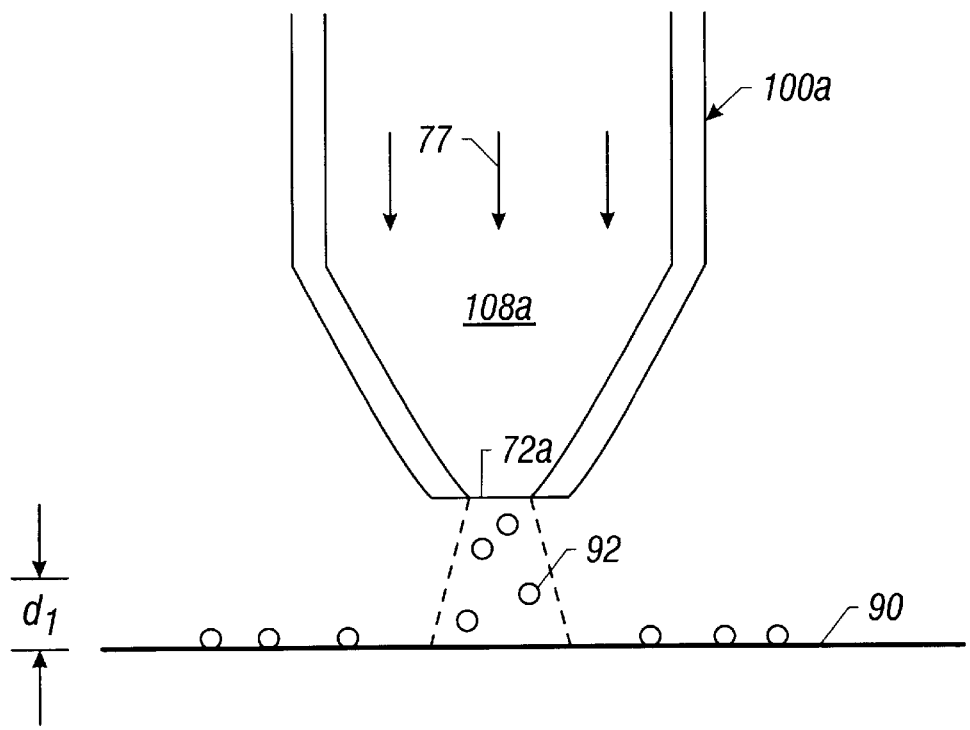
FIGS. 8A to 8D are schematic diagrams showing a method to avoid blocking the aperture of a probe with a quartz fiber.

A method for preventing blockage of the aperture of fiber optic probes is illustrated in FIGS. 8A–8D. As shown in FIG. 8A, tip 108a starts at a distance $d_1$ from surface 90.

Figure 8B:
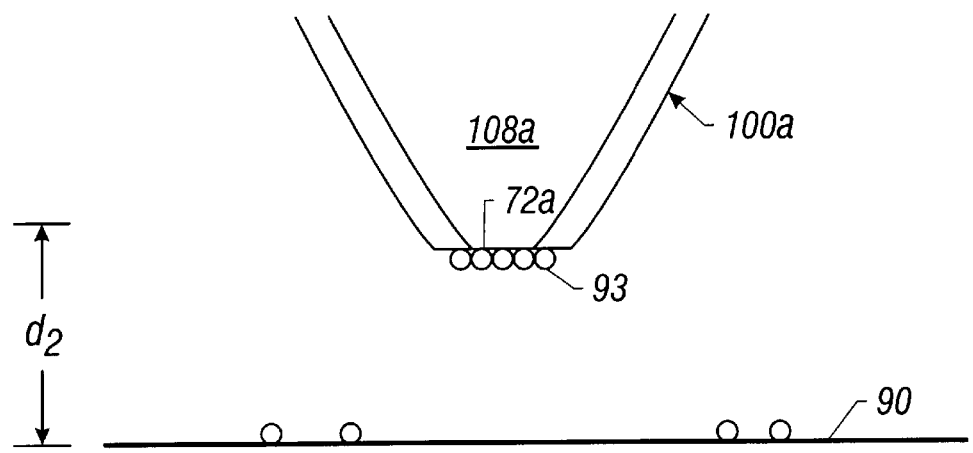
Figure 8C:
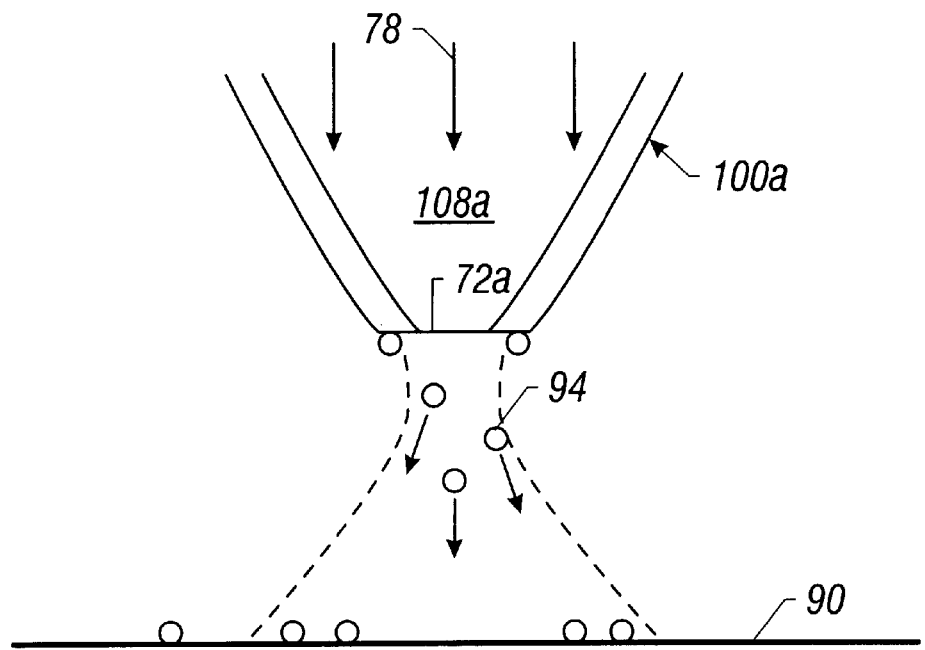
Figure 8D:
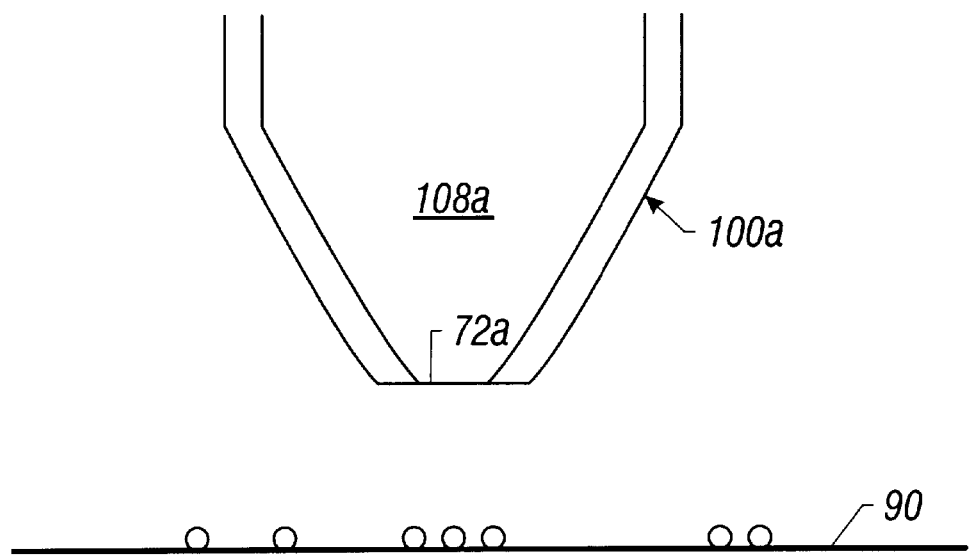

Distance $d_1$ should be less than the width of aperture 72a, as discussed above. Aperture 72a emits a light pulse 77 when the surface 90 is in the near-field zone. Light pulse 77 causes particles 92 to desorb from the surface, some of which attach to aperture 72a as shown in FIG. 8B. Tip 108a is then retracted from the surface 90 to a distance $d_2$ which is beyond the near-field zone. The distance $d_2$ between the tip and surface is selected so as to be large enough that the light spreads sufficiently that the spatial intensity of the light is too low to cause desorption from surface 90. After being retracted from the surface, another light pulse 78 is used to desorb ions 94 off aperture 72a, but not from the surface 90 (FIG. 8C). A distance of about one micron is appropriate to cause ions 93 to desorb from aperture 72a, but not from the surface. Finally, as shown in FIG. 8D, the probe is advanced so that the surface 90 is again in the near-field zone.

Once particles are desorbed from the surface, they may be analyzed to determine the composition of the material in question. In general, the particles are ionized by the light beam 77, and the ions are trapped by electric fields and funneled into analysis device 220 (FIG. 7). Device 220 may perform one or many forms of analysis, such as mass spectroscopy or optical spectrometry. To illustrate the principles of the invention, time of flight mass spectrometry (TOF-MS) is preferred because it is simple and has a high mass detection limit.

Figure 9:
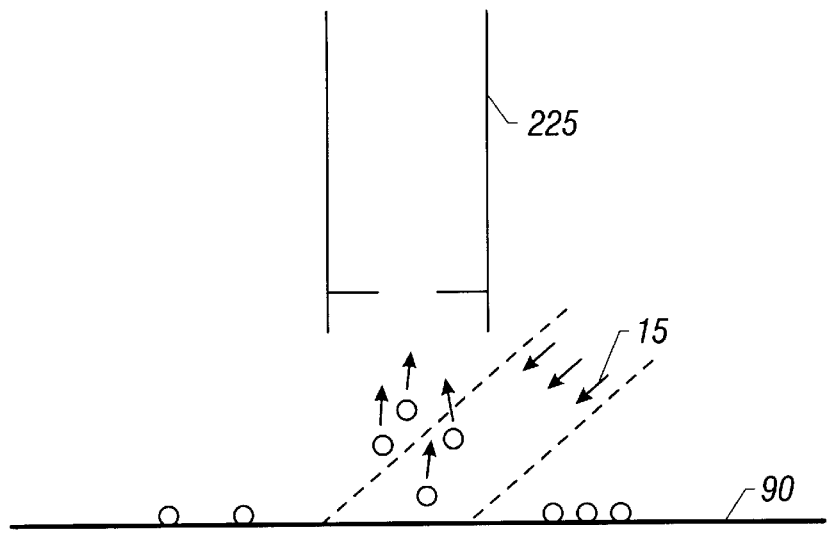
FIG. 9 is a schematic representation of the position of a flight tube according to the prior art.

FIG. 9 depicts a TOF-MS device according to the present invention. TOF-MS operates by separating ions of different mass-to-charge ratios based on their relative velocities when accelerated through a given electrostatic potential. When the particles are desorbed the ions formed are accelerated by an electrostatic field and are guided to detector plates. The flight time of the ions depends on their mass (Equation 1)

$$t = L/(2E/m)^{1/2} \quad (1)$$

wherein L is the length of the flight tube, E is the kinetic energy of the accelerated ion and m is the mass of the accelerated ion. Thus, the time position of the arrival of the ion relative to the laser pulse gives mass information.

The TOF-MS detection apparatus 220 includes a flight tube 280 and a ground plate 282. Ions 97 pass through a ring lens 285 which collimates the beam of ions. The ions then drift through a field-free region in the flight tube 280, where their different velocities separate them. At the end of the flight tube 280, the ions strike a detector 288. In one embodiment of the invention the ions are detected with a Micro Channel Plate (MCP) detector, purchased from Galileo Electro-Optics (Sturgbridge, Mass.). The amplified signal is delivered to a LeCroy 9450 oscilloscope and acquired by a computer using specialized software (TOFWARE, Ilys Software).

Figure 10:
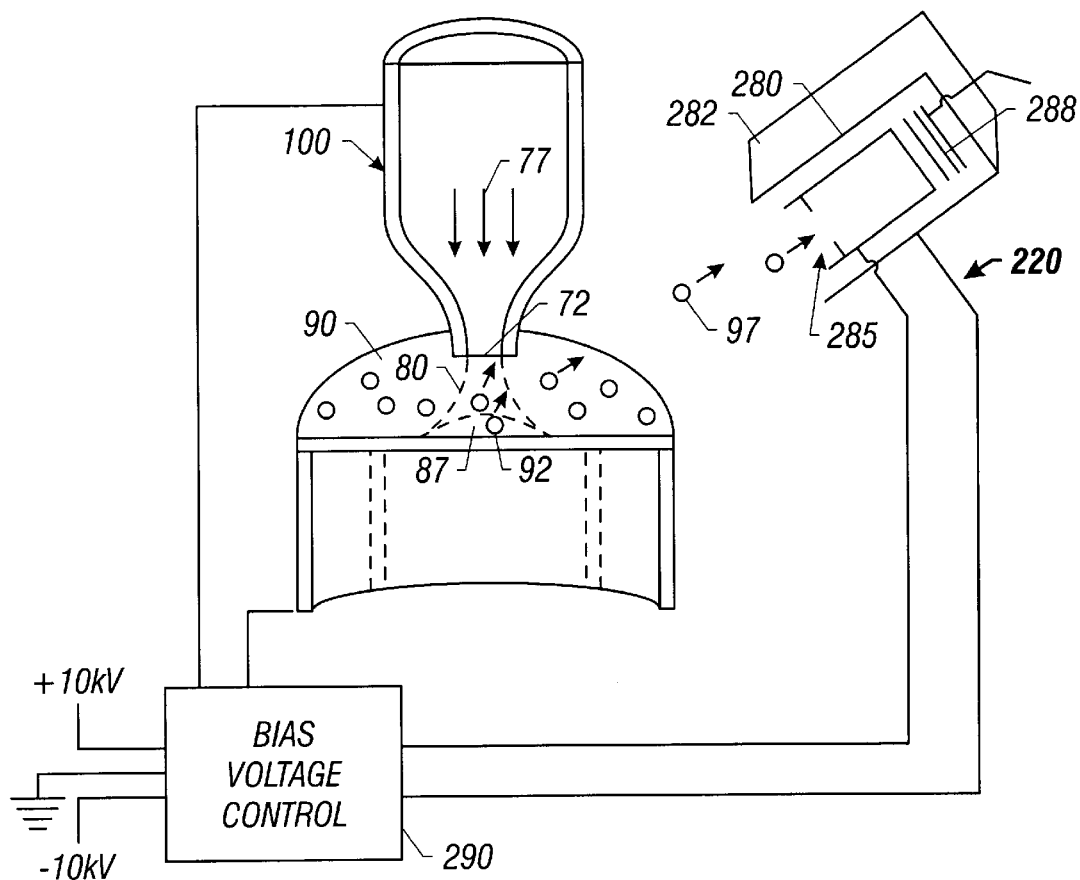
FIG. 10 is a sectional and schematic illustration of the piezoelectric scanner and flight tube according to the present invention.

As illustrated in FIG. 10, in prior art TOF-MS designs, the surface 10 is normal to the flight tube 225. Light beam 15 strikes surface 10 at an angle to cause particles 22 to desorb from spot 20. However, this prior art design cannot function with the desorption apparatus of the present invention. In the present invention, the aperture 72 must be normal to the surface 90, or else part of the desorption spot may not be in the near-field zone.

FIG. 9 illustrates the preferred embodiment in which the flight tube 280 is at a forty-five degree angle compared to the sample-probe assembly. The flight tube 280 may be at an angle between fifteen and seventy-five degrees, and more preferably between thirty and sixty degrees. Each of probe 100, sample 87, flight tube 280 and ground plate 282 is attached to a voltage bias voltage control 290 in order to apply a voltage bias. The bias voltage control 290 may connect to positive or negative voltage, or to a ground.

Several techniques may be used to create an electric field, which will funnel charged particles 97 into detector 288. In one embodiment, probe 100 and sample 87 are biased at positive ten kilovolts, and the tube 280 is negatively biased. However, it may be difficult to bias the entire probe 100 at a large voltage. It is preferred to ground sample 87 and probe 100, and bias the flight tube 280 at approximately negative three kilovolts. As positive ions 97 are desorbed, they are attracted to the negatively biased tube 280.

The present invention has been described in terms of a preferred embodiment. The invention, however, is not limited to the embodiment described and depicted. Rather, the scope of the invention is defined by the appended claims.

The following examples are provided for illustrative purposes only and are not intended to limit the scope of the invention.

EXAMPLES

The following examples illustrate laser desorption using fiber optic tips. In these examples the approach of the tip to the sample was visually monitored using a disectionscope focused through a window in the vacuum chamber wall onto the tip end. The distance between the tip and the sample was approximately $50\mu$, and therefore not in the near field zone. These examples illustrate that laser desorption is possible using fiber optic tips. Three samples were studied.

Figure 11:
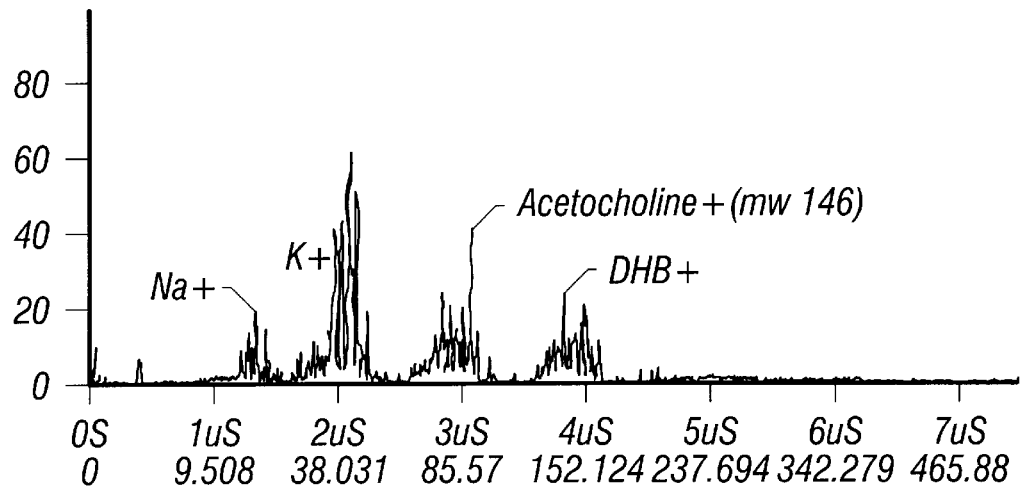
FIG. 11 illustrates the TOF mass spectrum of a sample of acetocholine in a dihydroxybenzoic matrix desorbed with a fiber optic tip.

Sample 1 was a solution of acetocholine (AC) in a dihydroxybenzoic acid (DHB) matrix. Sodium and potassium chloride were added for reference points in the mass spectrum. A drop of solution was placed on a copper plate and dried prior to desorption. The spectrum of this sample is depicted in FIG. 11. The resolution is high enough to resolve the AC and DHB peaks.

Samples 2 and 3 were obtained from Exon Research and Engineering Laboratories. These samples were stainless steel blocks with wear scars from tribology tests. Two different proprietary lubricants were used in these tests: FM-6 which contained an organometallic compound with molybdenum and HR-7, which did not have this additive.

Figure 12:
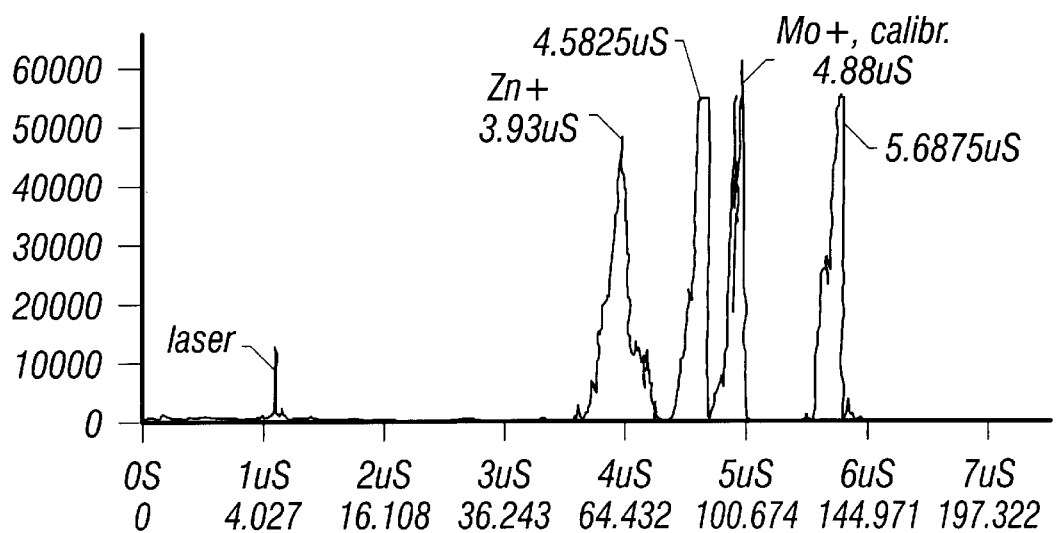
FIG. 12 illustrates the TOF mass spectrum of FM-6.
Figure 13:
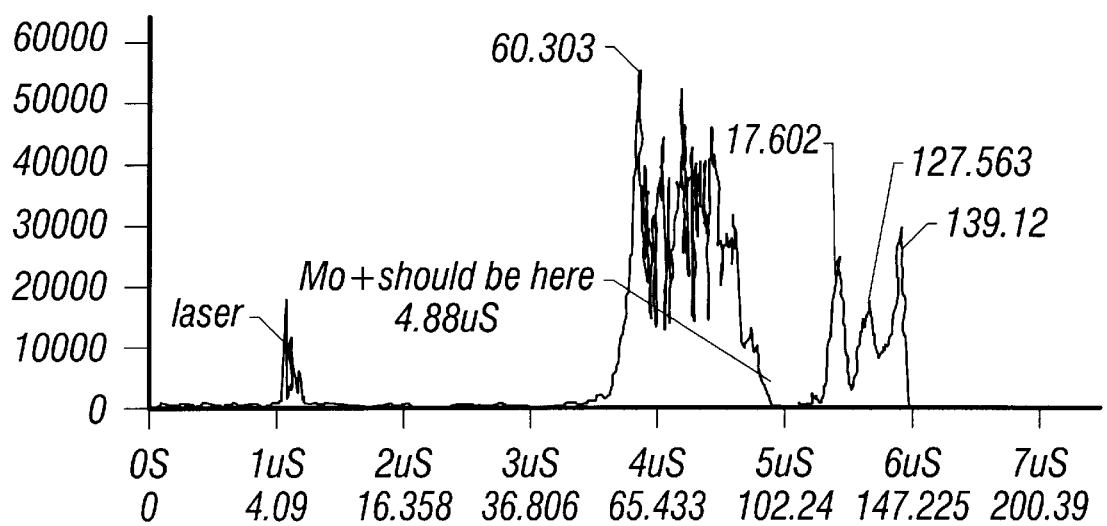
FIG. 13 illustrates the TOF mass spectrum of HR-7.

The probe was placed above the wear scar and the spectra were taken from this area. The spectra of these two samples is depicted in FIGS. 12 and 13. The arrival time of $Mo^+$ was calculated for reference. As can be seen in FIGS. 12 and 13 the FM-6 spectrum shows this peak at 4.88 $\mu S$ and the HR-7 peak does not.

What is claimed is:

1. A method of desorbing particles from a surface, comprising:

obtaining a near-field probe which is driven by a laser to produce an output light at an output aperture at an output end;

determining a near-field distance between said probe and the surface which will enable said probe to image in a near-field mode in which light output from the probe will remain collimated to approximately within a width of the output aperture;

adjusting an actual distance between the output end of the near-field probe and the sample to be analyzed, to keep said distance close to said near-field distance;

illuminating said sample using said probe, with an amount of energy effective to desorb particles from the surface of the surface;

wherein said laser is pulsed with an energy that is effective to desorb particles with each pulse; and a mass spectrometer device which has an element for sucking in particles that are desorbed, and further comprising pulsing said sucking and synchronizing the sucking of particles with pulses of the laser.

2. A method as in claim 1, wherein said laser is pulsed with an energy that is effective to desorb particles with each pulse.

3. A method as in claim 1, further comprising a mass spectrometer device with an input that receives particles which are desorbed by said laser.

4. A method as in claim 1, wherein said adjusting comprises electrically moving a mounting surface on which the sample is mounted, until the actual distance between the sample and the probe comes within said near-field distance.

5. A method as in claim 1, wherein said adjusting brings the tip of the probe to a distance approximately equal to a radius of the aperture.

6. A method as in claim 1, further comprising monitoring said actual distance, and maintaining said distance within a predesired amount, using a feedback loop.

7. A method as in claim 6, wherein said sample has an uneven topography, and further comprising moving said probe to a random position on said surface, and adjusting said actual distance to the near-field distance on said surface.

8. A method of determining characteristics of a sample of an uneven topography, comprising:

placing a sample having an uneven topography on a sample table;

moving a near-field probe to a random position on said sample;

positioning said probe and said sample to be spaced by a distance that is effective to allow said probe to transmit a light beam that impinges on said sample with a size substantially equal to or less than a size of an end of said probe;

illuminating said sample using said laser light pulses through said probe, with an energy that is effective to desorb particles from a surface of said sample;

sucking up said particles into a mass spectrometer to thereby determine a characteristic of said particles;

wherein said illuminating comprises pulsing said particles with said laser, each pulse causing particles to be desorbed;

wherein said sucking is carried out in a pulsed manner, pulses defining timing of said sucking being synchronized with a timing of said pulses to said laser, each pulse to said laser causing one suck by said mass spectrometer.

9. A method as in claim 8, wherein said illuminating comprises pulsing said particles with said laser, each pulse causing particles to be desorbed.

10. A method as in claim 8, wherein said distance is substantially a diameter of said probe.

11. An apparatus for determining chemical characteristics of a sample having an uneven topography, comprising:

a near-field probe;

a sample table, holding a sample to be investigated;

a moving element, moving a distance between said sample table and said probe to be within a near-field distance of said probe, in which an output of said probe has a spot size on said sample substantially equal to or smaller than an output diameter of said probe;

a controller, maintaining distance information about a current distance between said probe and said sample, to thereby hold said sample within said distance; and a mass spectrometer element, having a sucking portion, which sucks in particles which are desorbed by said laser element, and analyzes said particles to determine a characteristic thereof;

wherein said controller controls said laser beam in a pulsed mode, and said mass spectrometer sucks from said laser beam in said pulsed mode.

* * * * *